United States Patent [19]

Künstle et al.

[11] 3,997,550

[45] Dec. 14, 1976

[54] METHOD FOR THE PURIFICATION OF 2-AMINOTHIAZOLE

[75] Inventors: Gerhard Künstle, Raitenhaslach; Klaus Vornehm; Hellmuth Spes, both of Burghausen; Herbert Siegl, Haiming, all of Germany

[73] Assignee: Wacker-Chemie GmbH, Munich, Germany

[22] Filed: Apr. 10, 1975

[21] Appl. No.: 562,269

[30] Foreign Application Priority Data

Apr. 29, 1974 Germany .......................... 2420748

[52] U.S. Cl. ........................................ 260/306.8 R
[51] Int. Cl.² ........................................ C07D 277/40
[58] Field of Search ............................ 260/306.8 R

[56] References Cited

UNITED STATES PATENTS 2,600,620   6/1952   Crauland ................... 260/306.8 R Primary Examiner—Richard J. Gallagher
Attorney, Agent, or Firm—Hammond & Littell

[57] ABSTRACT

A method for the purification of crude 2-aminothiazole comprising subjecting an aqueous melt of crude 2-aminothiazole to a vacuum distillation in the presence of a trialkyl borate and fractional solidification of the ensuing vapors.

4 Claims, 1 Drawing Figure

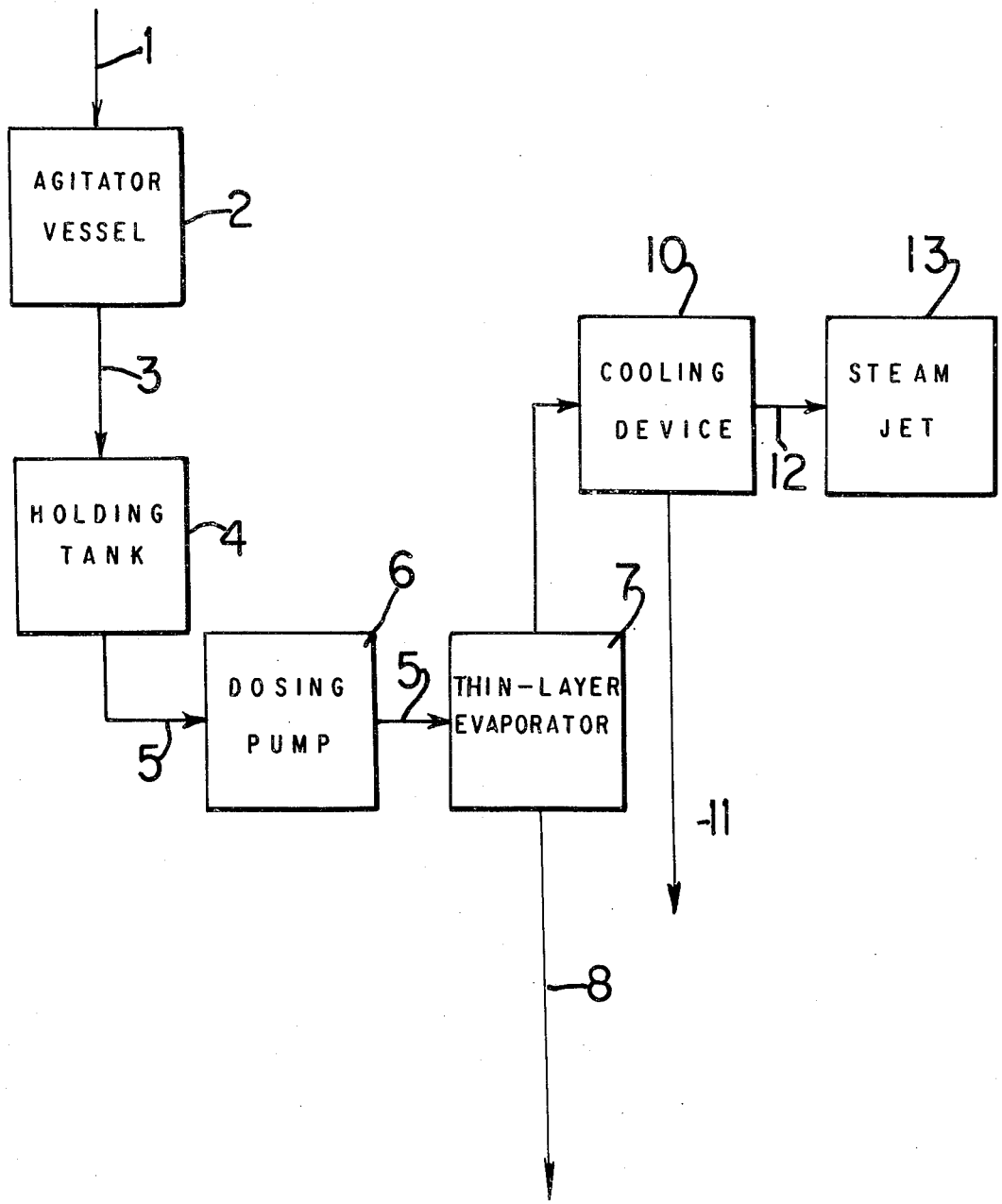

METHOD FOR THE PURIFICATION OF 2-AMINOTHIAZOLE

In all known methods for the production of 2-aminothiazole described in the literature, an impure product is obtained which must subsequently be subjected to refining or purification.

If the purification is effected by crystallization, repeated crystallizations under exclusion of air leads to pure 2-aminothiazole which, however, darkens greatly after a short time. In addition, this purification method leads to considerable losses of 2-aminothiazole and solvents.

In the purification by salt formation, for example, the sulfate, the sodium bisulfite compound, or the chloride, and crystallization, only the yield is reduced. A much improved product with regard to purity and color stability is not obtained.

Also, heretofore, distillation as a method of purification could only be carried out in the laboratory since it can lead to spontaneous decomposition of 2-aminothiazole.

An object of the present invention is to obtain 2-aminothiazole in a highly purified, color-stable form without decomposition.

Another object of the present invention is the development of a method for the purification of crude 2-aminothiazole comprising vacuum distilling an aqueous melt of 2-aminothiazole in the presence of a trialkyl borate, cooling the ensuing volatiles under fractional solidification conditions whereby 2-aminothiazole is primarily solidified, and recovering said purified 2-aminothiazole.

These and other objects of the invention will become more apparent as the description thereof proceeds.

The FIGURE is a flow-diagram of the process of the invention.

A method has now been found for purifying 2-aminothiazole by distillation. It is characterized in that crude 2-aminothiazole, as an aqueous melt, is subjected to vacuum distillation in the presence of a trialkyl borate, or a trialkyl ester of boric acid. Preferably a tri-lower alkyl borate is employed in an amount of from 0.005% to 0.3% by weight.

More particularly, the present invention relates to a method for the purification of crude 2-aminothiazole comprising vacuum distilling an aqueous melt of 2-aminothiazole in the presence of a trialkyl borate, cooling the ensuing volatiles under fractional solidification conditions whereby 2-aminothiazole is primarily solidified, and recovering said purified 2-aminothiazole.

The 2-aminothiazole prepared according to the known methods is usually obtained in water-moist form and can be purified by the present process directly in this form. A water-content of 10% to 20% by weight has proven to be particularly favorable, since the crude 2-aminothiazole can be transformed then into an aqueous melt at about 60° C. A higher water content should be avoided, however, because it reduces the purifying effect of the distillation.

It was found surprisingly that the stability of 2-aminothiazole, particularly against heat, is already greatly increased in the presence of small amounts of a trialkyl borate. This permits a safe distillative purification on a large scale, which leads to a product of high purity. Suitable trialkyl borates are all compounds whose boiling points are close to the boiling point of 2-aminothiazole under the conditions of the invention. A trialkyl borate has the general formula

$B(OR)_3$ wherein R denotes an alkyl, preferably a lower alkyl, with preferably 1 to 5 carbon atoms, where the groups R of a molecule can be the same or different. The alkyl is preferably methyl, ethyl, n-propyl, isopropyl, n-butyl, isobutyl, tert.-butyl, n-pentyl and isopentyl group. In addition, R can be alkenyl having from 3 to 5 carbon atoms such as allyl.

The trialkyl borate is preferably added during the melting of the water-moist solid crude base. Depending on the type of boric acid ester and the distillation conditions, from 0.005% to 0.3% by weight of boric acid ester, based on the crude base used, are generally sufficient.

It was also found that the stabilizing effect of the trialkyl borate can be increased or supplemented by the presence of small amounts of triphenyl phosphine. This co-stabilizer increases the stability of the 2-aminothiazole to air and light and makes it particularly stable against discoloration. The triphenyl phosphine is added to the crude base preferably together with the trialkyl borate in an amount of from 0.01% to 0.05% by weight. The addition of the triphenyl phosphine in the practice of the invention is optional and, therefore, it is added in an amount of from 0 to 0.05% by weight.

In general, the crude 2-aminothiazole containing stabilizers and co-stabilizers is refined at reduced pressure and elevated temperature by thin layer distillation. Pressures of 0.5 to 6 Torr, preferably 2 to 4 Torr, proved to be expedient. The evaporation temperature depends on the construction of the thin layer evaporator and on the vacuum applied. It is generally 150° C to 200° C. The boiling temperature of the water-moist crude base is determined, apart from the vacuum, by the water content and is about 92° C, for example, at 3.5 Torr and a water content of the crude base of 15.5%.

It its particulars, the invention, therefore, relates to a process for the purification of crude 2-aminothiazole consisting essentially of the steps of subjecting an aqueous melt of 2-aminothiazole in from about 10% to 20% by weight of water to vacuum distillation in the presence of from 0.005% to 0.3% by weight of a borate ester of the formula

$(B(OR)_3$ wherein R is a member selected from the group consisting of alkyl having from 1 to 5 carbon atoms, alkenyl having from 3 to 5 carbon atoms, and mixtures thereof, and from 0 to 0.05% by weight of triphenyl phosphine at a vacuum of from 0.5 to 6 Torr and a temperature of from 150° C to 200° C, cooling the volatiles produced to a temperature below the boiling temperature of 2-aminothiazole at the vacuum involved, and recovering said purified 2-aminothiazole.

All non-volatile portions are constantly removed from the thin layer evaporator in the form of solid residue capable of trickling, which can consist, for example, of common salt, sodium acetate and carbonaceous decomposition products, depending on the method by which the crude base is obtained, and which contains only small amounts of 2-aminothiazole. The volatile portions are fed to a cooling device, preferably at 10° C to 40° C, from which the pure 2-aminothiazole is continuously discharged in solid form by fractioned condensation and/or sublimation, while all other highly volatile impurities, particularly steam, are pumped off.

A continuous operation will be described on the basis of the drawing, which shows the schematic design of the distillation plant.

The solid, water-moist crude 2-aminothiazole base, trialkyl borate and, optionally, triphenyl phosphine, are fed through pipe 1 into the heatable agitator vessel 2. Therein, the mixture is heated under stirring to 60° C to 70° C, until a thinly liquid melt is obtained. The hot melt is fed through a short pipe 3 provided with a heating jacket to a heatable intermediate holding tank 4, which is kept at 65° C, and is conducted from tank 4 continuously by means of the heatable dosing pump 6 and the pipes 5, likewise provided with a heating jacket, to the thin layer evaporator 7 where it is evaporated in the vacuum and at elevated temperature. The dosing rate can be so selected that the non-volatile portions obtained from evaporator discharge line 8 contain as little 2-aminothiazole as possible and the non-volatiles are obtained as a tricklable solid. The volatile portion of the mixture evaporated in the thin layer evaporator, which consists particularly of 2-aminothiazole and water, as well as small am amounts of highly volatile by-products flow over the overflow pipe 9 and are fed to a self-cleaning cooling device 10. In the latter substantially only 2-aminothiazole is condensed and cooled to room temperature. The condensate or sublimate is constantly discharged from the vacuum condensor through pipe 11. All impurities which have not been condensed under the conditions of the method, particularly the steam, are fed through pipe 12 to the vacuum-producing steam jet unit 13.

The method according to the invention allows the purification of crude 2-aminothiazole safely by distillation on a technical scale. Beyond that, in contrast to all presently known purification methods, a particularly pure light-colored 2-aminothiazole is obtained in a high yield in one step, which is stable against discoloration.

2-Aminothiazole is used as an important base for numerous reactions: in the pharmaceutical industry, for example, in the preparation of the sulfonamide, sulfathiazole; in the dye industry for the preparation of azo dyes; and, finally, due to its physiological effect even as an additive to feed in some countries.

The following examples are illustrative of the practice of the invention without being limitative in any respect.

EXAMPLE 1

A distillation according to the schematic flow diagram of the FIGURE was employed.

The agitator vessel 2 was discharged through pipe 1 with: 50 kg of solid 2-aminothiazole crude base, containing 70% by weight of 2-aminothiazole, 15.5% by weight of water, 4.6% by weight of common salt, and 9.7% by weight of impurities of an unknown nature;
 50 gm of tributyl borate; and
 5 gm of triphenyl phosphine.

This mixture was heated under stirring to 65° C, and a thinly liquid dosable melt was obtained which was discharged while maintaining this temperature, into the intermediate holding tank 4 and fed from there by means of the dosing pump 6 at a rate of 7.1 l/h, corresponding to 10 kg/h, to the thin layer evaporator 7, which, like the cooling device 10, was under a vacuum of 3.5 Torr. The heating jacket of the thin layer evaporator 7 was maintained at 180° C and the cooling of the jacket of the cooling device 10 was maintained at 25° C. 0.76 kg of tricklable carbonaceous residue were discharged per hour from the vacuum through line 8, which contained 60.5% common salt. In addition to 8.2% of 2-aminothiazole, which was discarded, 9.2 kg of a mixture consisting of 2-aminothiazole, water and highly volatile by-products per hour distilled and sublimated at 92° C over the overflow pipe 9 into the cooling device 10. In the cooling device 10, maintained at 25° C, the 2-aminothiazole was condensed from the volatile mixture and discharged continuously in solid form through line 11. 6.4 kg of crystalline, 97.8% pure 2-aminothiazole with a water content of less than 0.1% were obtained per hour.

The melting point of the pure product was 90° C and the color value was 28% absorption. The absorption in per cent of a 3% ethanol solution in a layer thickness of 1 cm was measured by means of a filter photometer (Elko II by Zeiss) by using the color filter S 45 E (Zeiss product). No discoloration was observed during a period of 6 weeks.

EXAMPLE 2

Example 1 was followed with the exception that 25 gm of triethyl borate were used as the trialkyl borate. A correspondingly pure product was obtained. No discoloration was observed during a period of 6 weeks.

EXAMPLE 3

Example 1 was followed with the exception that 50 gm of tri-n-propyl borate were used as the trialkyl borate. Here too, a correspondingly pure product was obtained and no discoloration was observed during a period of 6 weeks.

EXAMPLE 4

Example 1 was followed with the exception that 100 gm of tripentyl borate were used as the trialkyl borate. Again a correspondingly pure product was obtained and no discoloration was observed during a period of 6 weeks.

EXAMPLE 5

Example 1 was followed with the exception that the distillation was effected without the co-stabilizer, triphenyl phosphine. Again a correspondingly pure product was obtained, but after 3 to 6 weeks a darker coloration of the initially light-colored distilled 2-aminothiazole was observed on the surface which had been exposed to light and air.

The preceding specific embodiments are illustrative of the practice of the invention. It is to be understood, however, that other expedients known to those skilled in the art or described herein may be employed without departing from the spirit of the invention or the scope of the appended claims.

We claim:

1. A process for the purification of crude 2-aminothiazole consisting essentially of the steps of subjecting an aqueous melt of 2-aminothiazole in from about 10% to 20% by weight of water to vacuum distillation in the presence of from 0.005% to 0.3% by weight of a borate ester of the formula $$B(OR)_3$$

wherein R is a member selected from the group consisting of alkyl having from 1 to 5 carbon atoms, alkenyl having from 3 to 5 carbon atoms, and mixtures thereof, and from 0 to 0.05% by weight of triphenyl phosphine at a vacuum of from 0.5 to 6 Torr and a temperature of from 150° C to 200° C, cooling the volatiles produced to a temperature below the boiling temperature of 2-aminothiazole at the vacuum involved, and recovering said purified 2-aminothiazole.

2. The process of claim 1 wherein said vacuum is from 2 to 4 Torr.

3. The process of claim 1 wherein said volatiles are cooled at a temperature between 10° C and 40° C at the vacuum involved.

4. The process of claim 1 wherein said triphenyl phosphine is present in an amount of from 0.01% to 0.05% by weight as a co-stabilizer.

* * * * *